United States Patent
Uihlein

(10) Patent No.: US 11,337,721 B2
(45) Date of Patent: May 24, 2022

(54) FLEXIBLE THREE-ARM SNARE STRUCTURE AND A METHOD OF USING THE FLEXIBLE THREE-ARM SNARE STRUCTURE TO RETRIEVE STONES FROM A HUMAN BODY

(71) Applicant: Coloplast A/S, Humlebaek (DK)

(72) Inventor: Bernhard Uihlein, Dettingen (DE)

(73) Assignee: Coloplast A/S, Humlebaek (DK)

( * ) Notice: Subject to any disclaimer, the term of this patent is extended or adjusted under 35 U.S.C. 154(b) by 588 days.

(21) Appl. No.: 16/413,639

(22) Filed: May 16, 2019

(65) Prior Publication Data

US 2019/0262026 A1 Aug. 29, 2019

Related U.S. Application Data

(63) Continuation of application No. 15/306,768, filed as application No. PCT/DK2015/050110 on Apr. 29, 2015, now Pat. No. 10,335,185.

(30) Foreign Application Priority Data

Apr. 30, 2014 (DE) ..................... 10 2014 208 168.8

(51) Int. Cl.
| | |
|---|---|
| *A61B 17/3205* | (2006.01) |
| *A61B 17/221* | (2006.01) |
| *A61B 17/00* | (2006.01) |

(52) U.S. Cl.
CPC ...... *A61B 17/32056* (2013.01); *A61B 17/221* (2013.01); *A61B 2017/00358* (2013.01); *A61B 2017/2215* (2013.01)

(58) Field of Classification Search
CPC .......... A61B 17/221; A61B 2017/2215; A61B 2017/2212; A61B 17/32056; A61B 2017/00867; A61B 10/0266; A61B 17/22031; A61F 2002/016; A61F 2230/005; A61F 2230/0076
See application file for complete search history.

(56) References Cited

U.S. PATENT DOCUMENTS

2015/0196311 A1* 7/2015 Chu ..................... A61B 17/221
606/127

* cited by examiner

*Primary Examiner* — Katherine M Shi
(74) *Attorney, Agent, or Firm* — Coloplast Corp., Coloplast A/S; Nick Baumann

(57) ABSTRACT

An endoscopic instrument provides a flexible three-arm snare structure that is adapted to retrieve stones from a human body.

9 Claims, 11 Drawing Sheets

Figure 1:
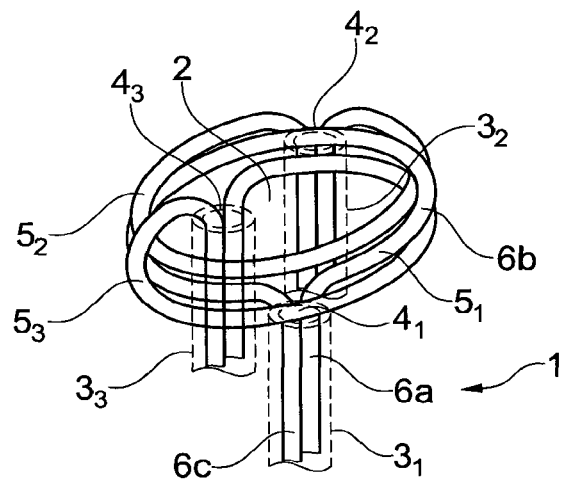

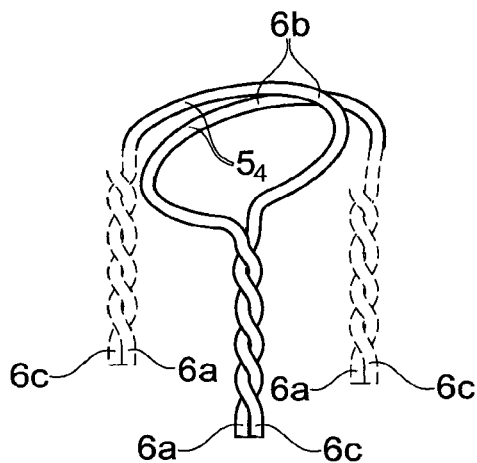
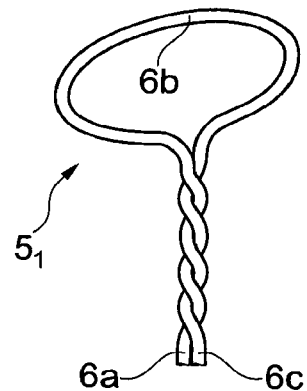
Fig. 13         Fig. 14
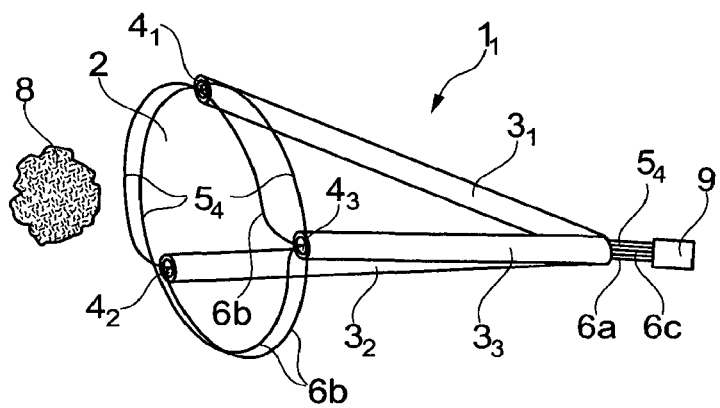
Fig. 15
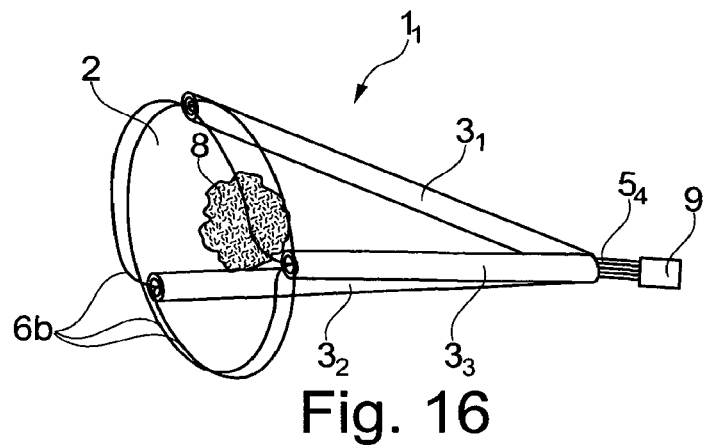
Fig. 16

FLEXIBLE THREE-ARM SNARE STRUCTURE AND A METHOD OF USING THE FLEXIBLE THREE-ARM SNARE STRUCTURE TO RETRIEVE STONES FROM A HUMAN BODY

The invention relates to a snare instrument according to the preamble of Claim 1. Snare instruments of this kind can be used in particular as medical snare instruments in order to remove foreign bodies, blood clots, stones or other concretions from human or animal tissues or in order to trap them, preferably using a corresponding endoscopic catheter instrument. For this purpose, in the opened position of the snare structure, the object to be trapped is brought through the distal snare opening into the snare and is held securely therein by means of the snare structure being pulled closed. The closing action is initiated by axially pulling back the noose wires, of which the distal noose arches thereby shorten, such that the distal ends of the flexible bending tubes move radially towards each other. When the noose wires are moved axially forwards again, their distal noose arches lengthen again, and the flexible bending tubes, and therefore the snare structure as a whole, return elastically again to their opened starting position.

The technical problem addressed by the invention is that of making available a snare instrument which is of the type mentioned at the outset and which, compared to conventional snare instruments, has an improved snaring function and can be produced at relatively low cost.

The invention solves this problem through the provision of a snare instrument according to Claim 1. In one embodiment, the noose arch of at least one of the noose wires extends, with a circumferential length of at least two bending tube circumferential spacings, in the circumferential direction of the snare structure. This means that the noose arch does not extend from one bending tube directly to an adjacent bending tube, but instead at least to a next but one bending tube in the circumferential direction of the snare structure, although it can also extend over the entire circumferential length of the snare structure by 360°, by being looped back to the same bending tube from which it emerges, or by even more than 360°. In one embodiment, several noose arches extend, with this circumferential length of at least two bending tube circumferential spacings, in the circumferential direction of the snare structure, and it can be advantageous if the noose arches of all the noose wires extend, with this circumferential length of at least two bending tube circumferential spacings, in the circumferential direction of the snare structure.

The snare instrument permits particularly favourable snaring functions, which means that objects such as foreign bodies, blood clots, stones and other concretions in human or animal tissues can be reliably trapped and held secure. Moreover, the snare instrument can be produced at relatively low cost. Other advantageous embodiments of the invention are set forth in the dependent claims.

In one embodiment, the noose arches form an intersecting noose structure, in which at least one noose arch extends in a first portion in front of a first other noose arch and extends in a second portion behind the first other noose arch or behind a second other noose arch. An intersecting noose structure of this kind permits the formation of a knot-like closure of the distal end of the snare structure when the latter is pulled closed. Moreover, the intersecting noose structure is such that a particle that is to be trapped can be more easily detached from a tissue wall as a result of the shearing effect of the intersecting noose arch portions.

In one embodiment, both base portions of at least one of the noose wires are arranged so as to be axially movable in the same direction and in synchrony. For the snare structure to be pulled closed or contracted, it is then possible for both base portions of the relevant noose wire to be pulled in the same direction and in synchrony, such that the distal noose arch of the noose wire shortens uniformly on both arch sides. Advantageously, the two base portions of several or all of the noose wires are arranged in this way so as to be axially movable in the same direction and in synchrony. Alternatively, of the two base portions of at least one noose wire, only one is arranged so as to be axially movable, while the other base portion remains axially immovable, e.g. by axially immovable coupling to an outer casing of the shaft area or to another component of the snare instrument that remains axially unmoved when the snare structure is contracted.

In one embodiment, several noose wire base portions extend axially movably in the same direction and in synchrony in at least one bending tube. Advantageously, several noose wire base portions, e.g. two of them, can in this way extend axially movably in the same direction and in synchrony in several or all of the bending tubes. Alternatively, at least one of several noose wire base portions extending in a bending tube can be arranged to be axially unmoved.

In one embodiment, the noose arch of at least one of the noose wires extends, in the circumferential direction of the snare structure, with a circumferential length that is equal to the circumferential length of the snare structure. In other words, the noose arch extends over the entire circumferential length of the snare structure and then returns, for example, back into the bending tube from which it emerges. This provides a full 360° noose at the distal end of the snare structure. Advantageously, the noose arch of several or all of the noose wires can extend with this full circumferential length of the snare structure.

In one embodiment, at least two of the noose wire base portions extend, connected to each other, in at least one of the bending tubes. The connection can, for example, involve the base portions being intertwined and/or welded together and/or bonded together. In suitable uses, this can improve the stability of the noose wires in their base portions and can facilitate an axial movement, in the same direction and in synchrony, of the noose wire base portions guided in a respective bending tube.

In one embodiment, at least one of the bending tubes is formed by a helical spring tube. This represents one advantageous configuration of the bending tubes. Advantageously, several or all of the bending tubes are formed in this way by a helical spring tube. Alternatively, at least one of the bending tubes is formed in another way, for example from a monofilament hollow wire material.

In one embodiment, exactly one noose wire base portion extends in at least one of the bending tubes. Thereby, the bending tube needs only to receive a single noose wire base portion and can therefore be produced, for example, with a relatively small diameter. Since only a single noose wire base portion is present in the bending tube, no difficulties arise from interactions between several noose wire base portions extending in a bending tube, e.g. frictional effects in cases where at least one of the noose wire base portions extending in a bending tube is moved axially in order to contract the snare structure, while at least one other noose wire base portion remains axially immovable in the bending tube.

In one embodiment, the noose wires extend proximally as far as a connection site at which they are coupled to a distal end of a pull rod which extends all the way through the shaft area to a proximal control area of the instrument. In this embodiment, the snare structure is actuated with the aid of the pull rod on the shaft side.

In one embodiment, the noose wires extend proximally all the way through the shaft area as far as a proximal control area of the instrument. In this embodiment the noose wires, with their base portions extending as far as the proximal control area of the instrument serve as transmission elements for the tensile force for contracting the snare structure.

In one embodiment, the snare structure has a flexible snaring net structure, which is arranged in the snaring space formed by the bending tubes and is held on the bending tubes. For certain uses, the snaring net structure further improves the snaring properties of the snare instrument.

Figure 2:
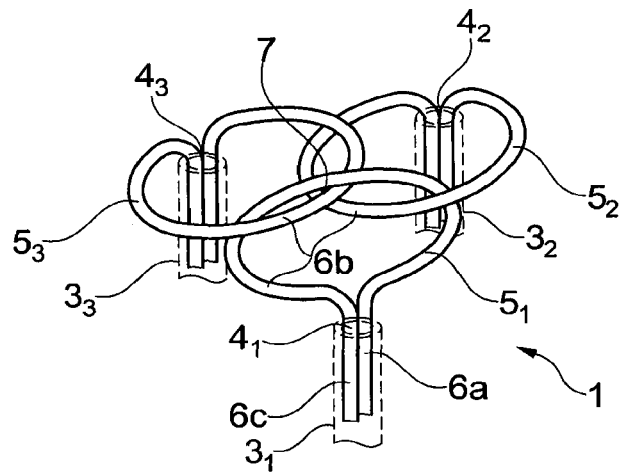
Figure 3:
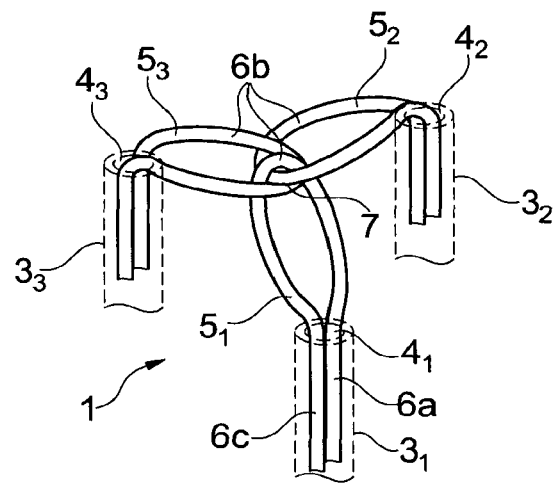
Figure 4:
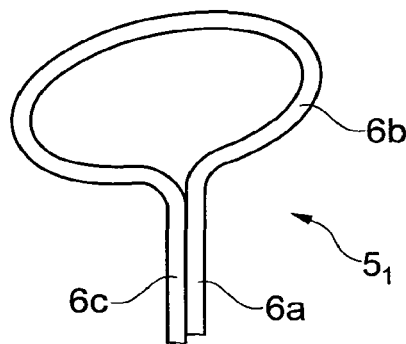
Figure 5:
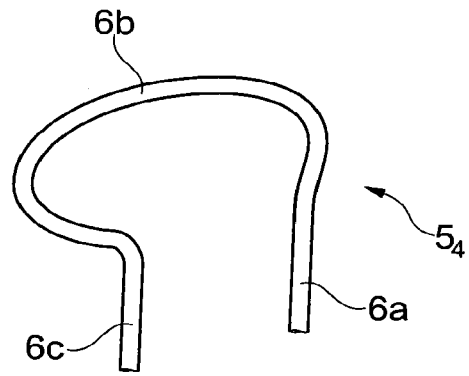
Figure 6:
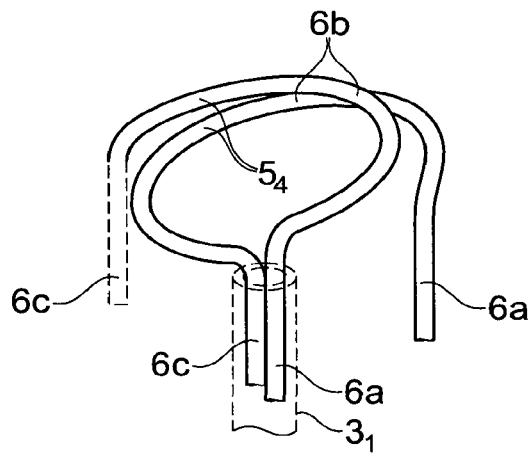
Figure 7:
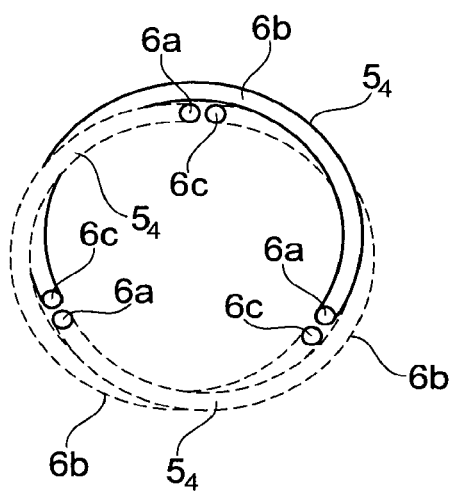
Figure 8:
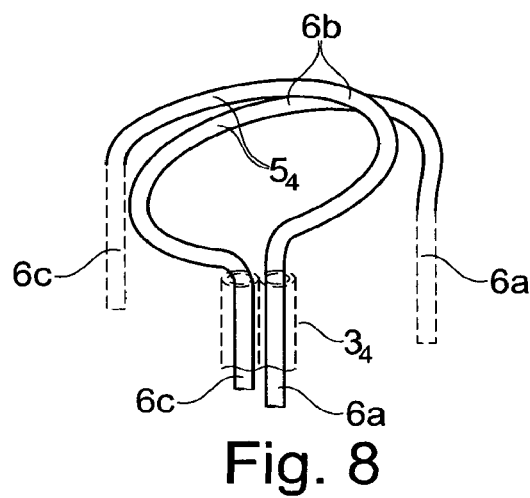
Figure 9:
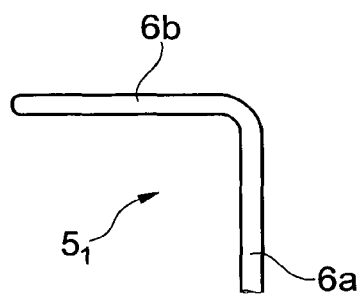
Figure 10:
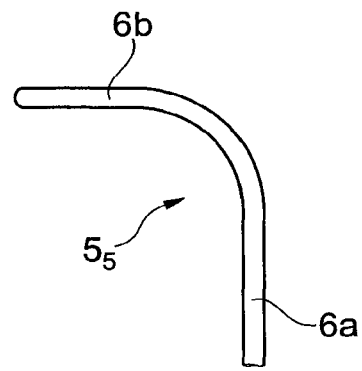
Figure 11:
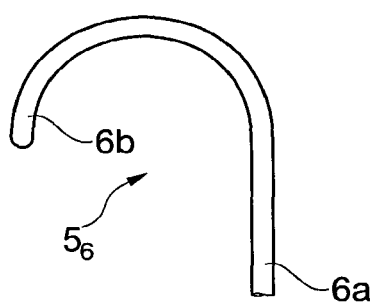
Figure 12:
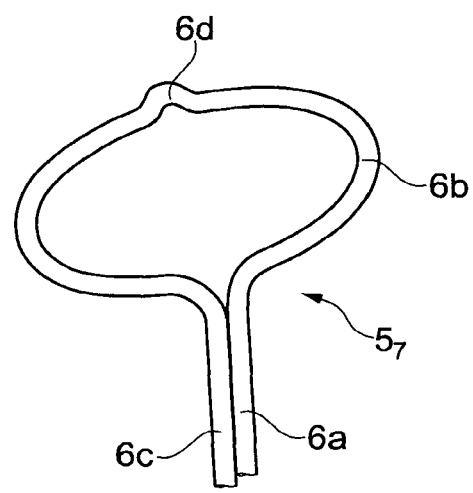
Figure 17:
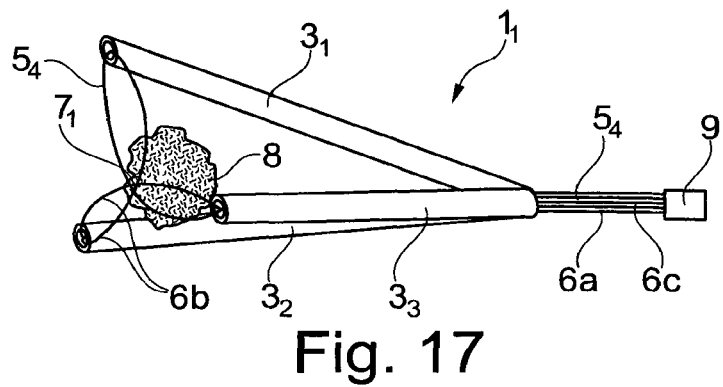
Figure 18:
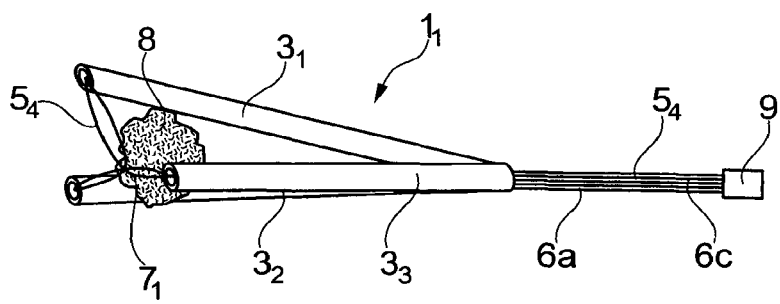
Figure 19:
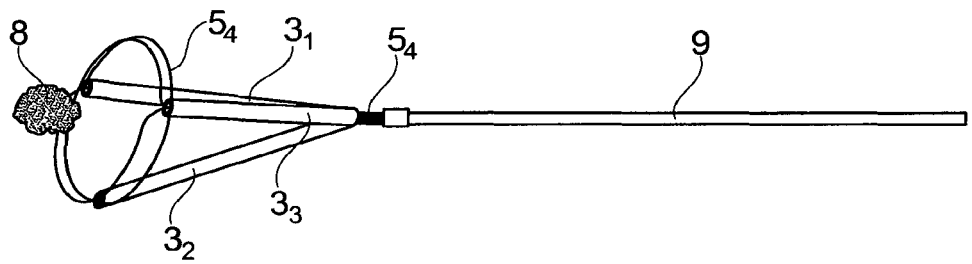
Figure 20:
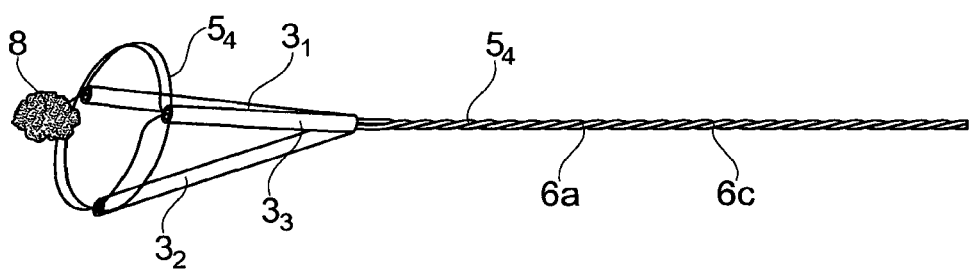
Figure 21:
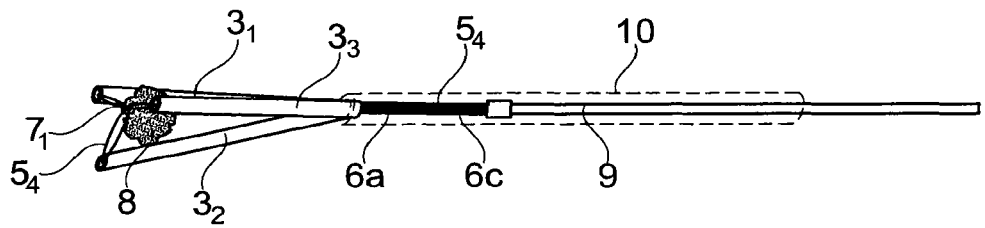
Figure 22:
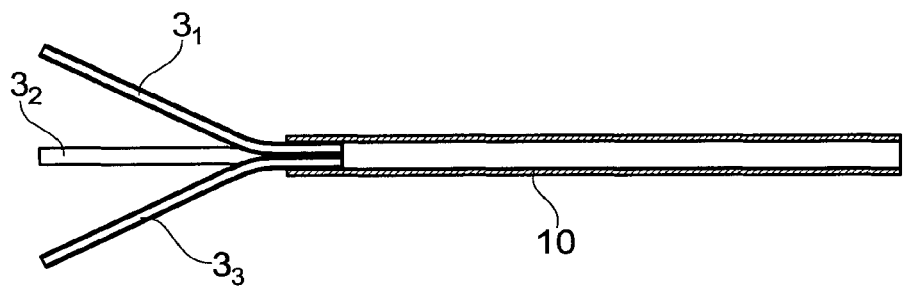
Figure 23:
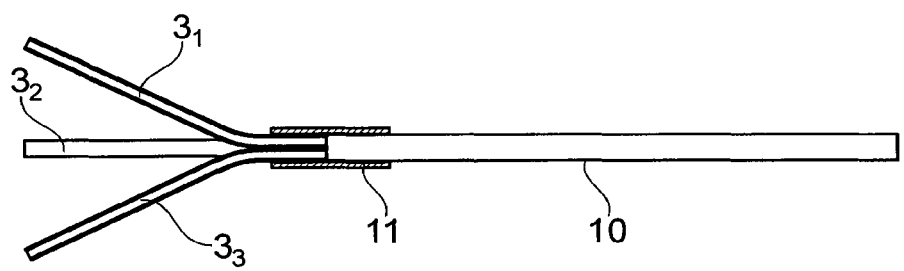
Figure 24:
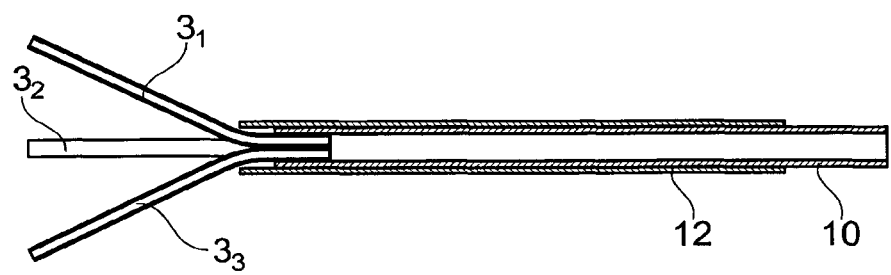
Figure 28:
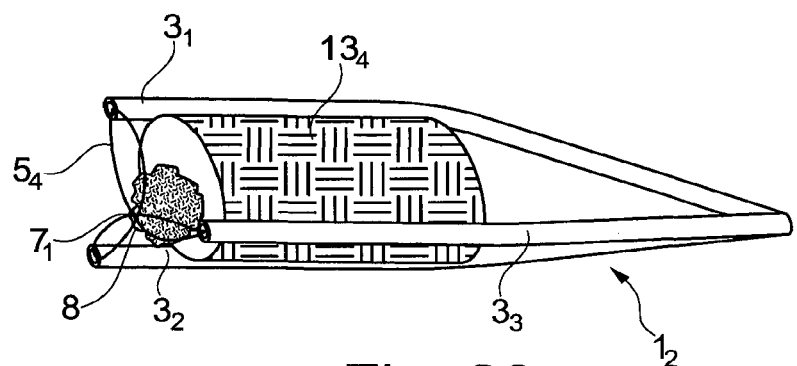
Figure 29:
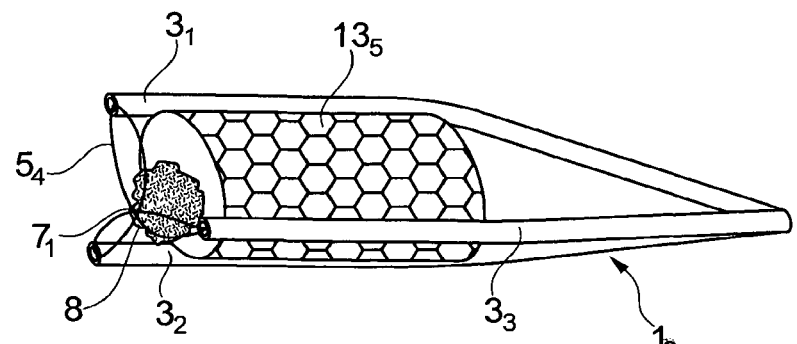
Figure 30:
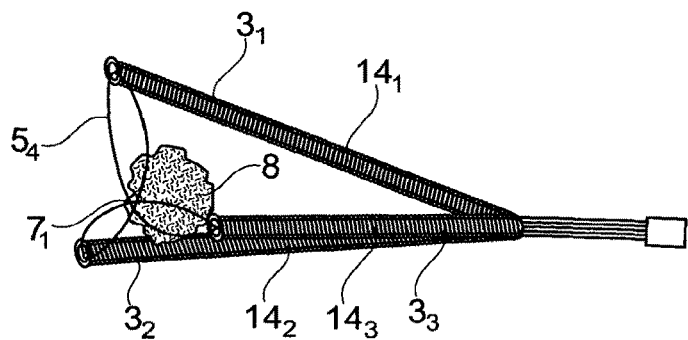
Figure 31:
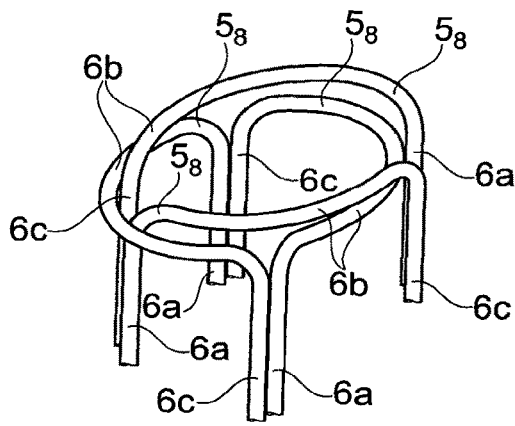
Figure 40:
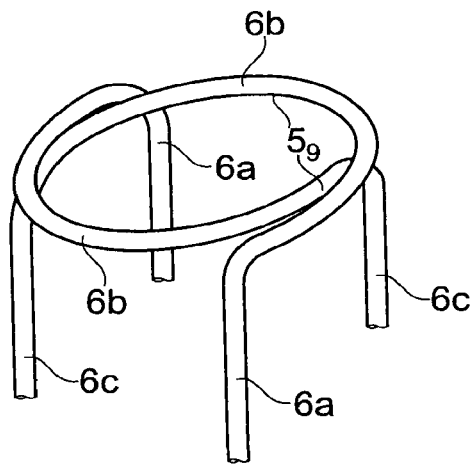
Figure 41:
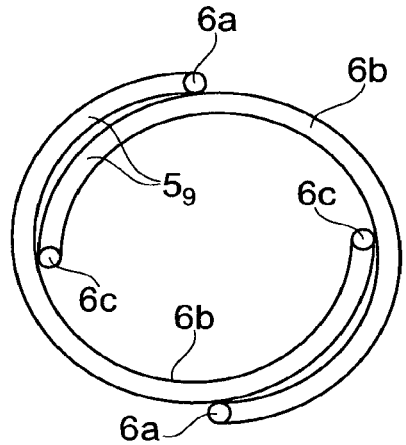
Figure 42:
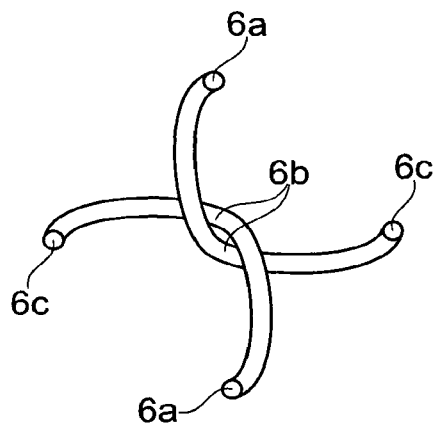
Figure 43:
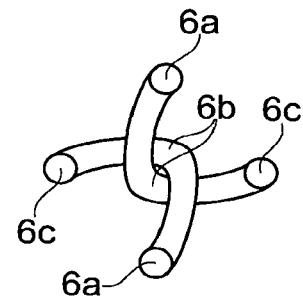
Figure 44:
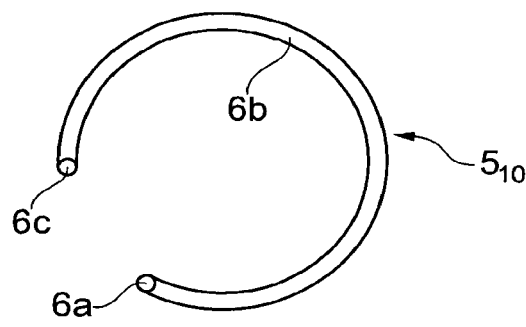
Figure 45:
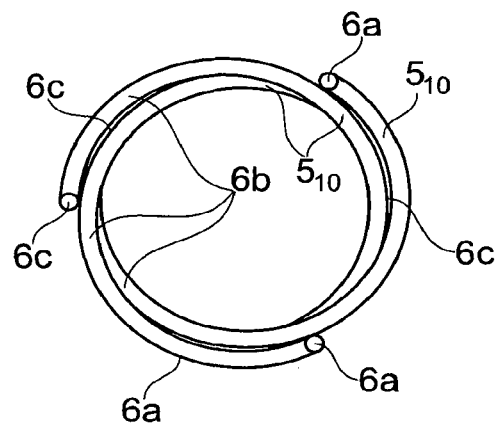
Figure 46:
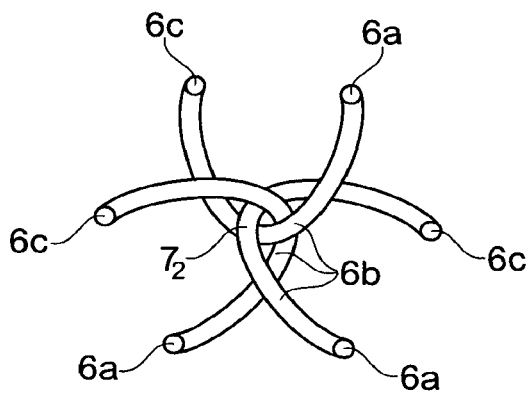
Figure 47:
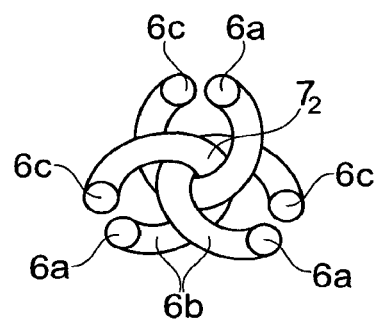
Figure 48:
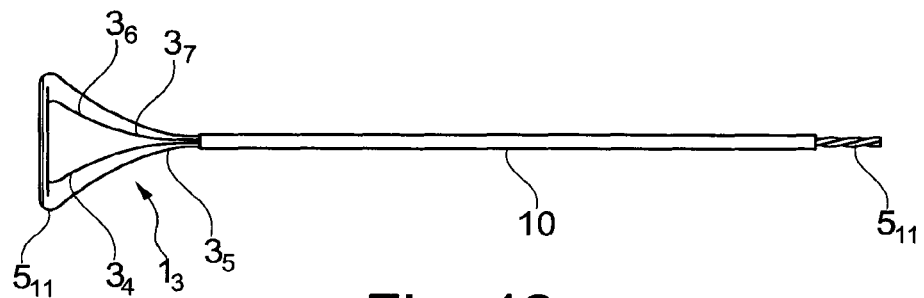
Figure 49:
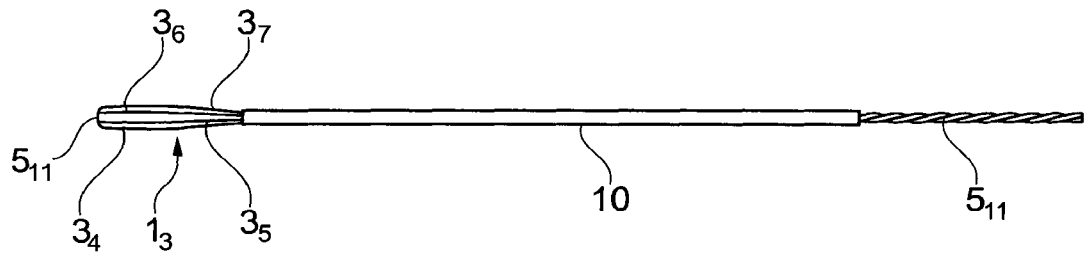
Figure 50:
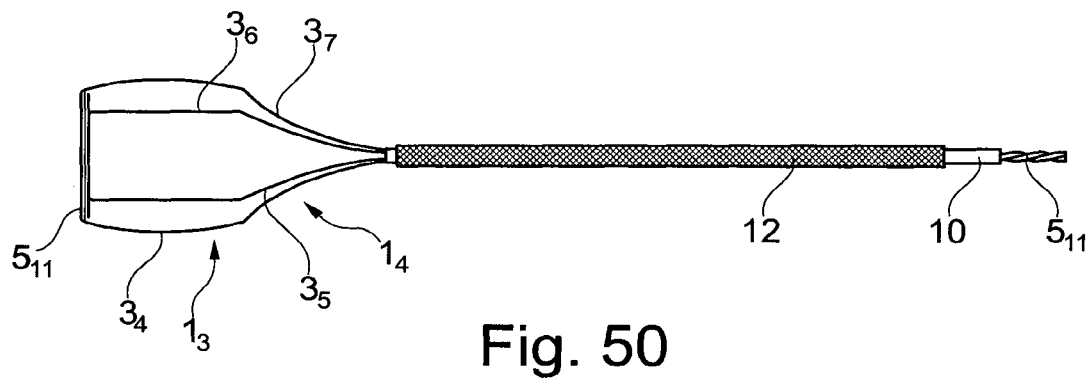
Figure 51:
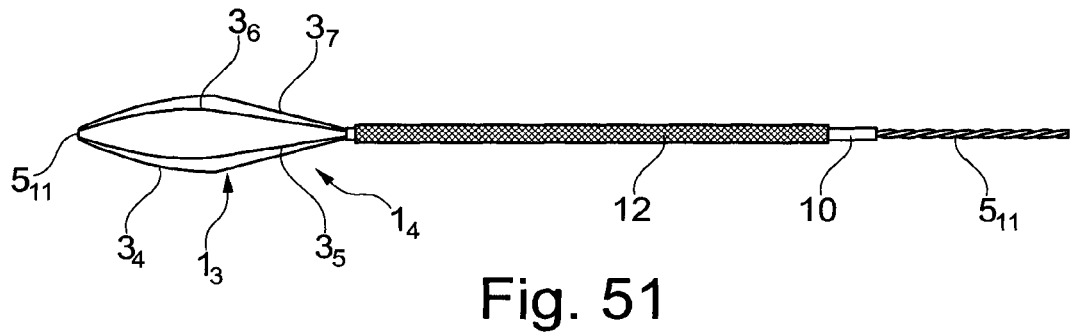
Figure 52:
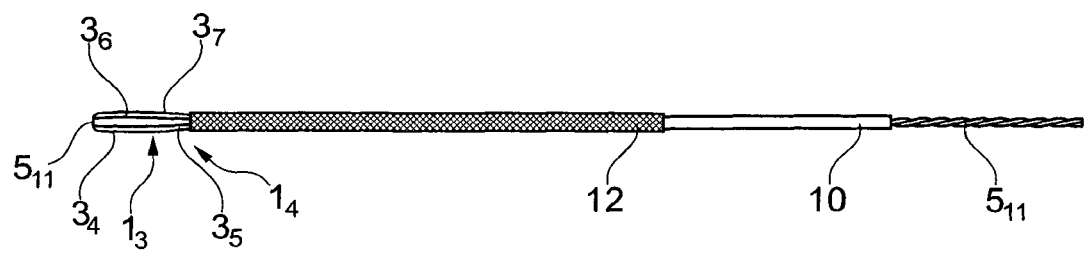

Advantageous embodiments of the invention are further described below and are depicted in the drawings, in which:

FIG. 1 shows a schematic perspective view of one embodiment of a snare structure with three bending tubes and with three intersecting noose arches extending over the full circumferential length of the snare in the opened position, FIG. 2 is similar to FIG. 1 and shows the snare structure in a slightly contracted position, FIG. 3 is similar to FIGS. 1 and 2 and shows the snare structure further contracted, FIG. 4 is a schematic perspective view of a distal portion of one of the three noose wires used in the snare structure according to FIGS. 1 to 3, FIG. 5 is a perspective view of one embodiment of a distal portion of a noose wire for a further snare structure with three bending tubes, FIG. 6 is a schematic perspective view which depicts two of three noose wires of FIG. 5 for one embodiment of a snare structure with three bending tubes, FIG. 7 is a plan view of one embodiment of the snare structure with three noose wires according to FIG. 5 in the manner of FIG. 6, FIG. 8 is a perspective view of one embodiment of a snare structure with double-lumen bending tubes, FIG. 9 is a schematic side view of the distal portion of the noose wire of the embodiment of FIG. 4, FIGS. 10 and 11 are side views of other embodiments of noose wire variants, FIG. 12 is a perspective view of one embodiment of a noose wire, FIG. 13 is a schematic perspective view of a variant with twisting of the noose wire base portions in the respective bending tube, FIG. 14 shows a perspective view of a noose wire variant with twisted base portions, FIGS. 15 to 18 are perspective side views of a snare structure of the embodiments of FIGS. 5 to 7, in a sequence during which a particle is snared, FIGS. 19 and 20 are perspective side views showing two further variants of the shaft area, FIG. 21 is a perspective side view similar to FIG. 18 showing a larger portion of the shaft area, FIGS. 22 to 24 are longitudinal sectional views of one embodiment of a snare instrument illustrating different ways of securing the snare structure on the shaft area, FIGS. 25 to 29 are perspective views of various embodiments of snare structures with different additional snaring net structures, FIG. 30 is a perspective side view of one embodiment with helical spring bending tubes, FIG. 31 is a perspective view of one embodiment of a snare structure and noose wire arrangement with four noose arches that each extend around half the circumference of the snare in a non-intersecting arrangement, FIGS. 32 to 35 are plan views of the noose arch arrangement of FIG. 31 in increasingly contracted positions, FIGS. 36 to 39 are plan views of one embodiment with the noose arches in an intersecting arrangement and in increasingly contracted positions, FIG. 40 is a perspective view of one embodiment with only one noose wire base portion per bending tube, FIGS. 41 to 43 are plan views of the noose arch arrangement of FIG. 40, in increasingly contracted positions, FIG. 44 is a plan view of one embodiment of a distal noose arch of a noose wire for a snare structure with six bending tubes, FIGS. 45 to 47 are plan views of the snare structure with the noose wires according to the embodiment of FIG. 44, FIGS. 48 and 49 are side views of one embodiment of a snare instrument with a funnel-shaped snare structure, in the opened and contracted positions, respectively, and FIGS. 50 to 52 are side views of one embodiment of a snare instrument with a bulbous snare structure in the opened, half contracted and fully contracted positions, respectively.

The disclosure relates to a snare instrument in which a snaring area distally adjoins a shaft area which has an elastically foldable snare structure serving to trap objects, and, particularly when the snare instrument is used as a medical snare instrument, the objects to be trapped can be foreign bodies, stones, concretions and other particles that are intended to be removed endoscopically from human or animal tissues. FIGS. 1 to 3 show a first illustrative embodiment of such a snare structure 1 which, in the opened position shown in FIG. 1, forms a snare with a trap opening 2 lying at the front, and which can be contracted elastically from the opened position. FIGS. 2 and 3 show the snare structure 1 in successively more contracted positions.

In the example shown in FIGS. 1 to 3, the snare structure 1 comprises three bending tubes $3_1$, $3_2$, $3_3$ which, in the circumferential direction of the snare structure 1, are arranged equidistantly from each other at a circumferential spacing of in each case 120°. The bending tubes $3_1$, $3_2$, $3_3$ consist of a flexible metal or plastic material and, in the opened position of the snare structure, extend distally forwards and radially outwards in a radiating shape to form the snare. Furthermore, their distal ends $4_1$, $4_2$, $4_3$ can be moved radially inwards towards each other so as to pull the snare structure 1 closed.

To permit this closing movement, three noose wires $5_1$, $5_2$, $5_3$ are provided, each of which extends with a first base portion 6a from a shaft area (not shown) of the instrument loosely through one of the bending tubes $3_1$, $3_2$, $3_3$ as far as the distal end $4_1$, $4_2$, $4_3$ thereof, from there with a noose arch 6b to the distal end $4_1$, $4_2$, $4_3$ of the same bending tube $3_1$, $3_2$, $3_3$, and from there with a second base portion 6c loosely through the latter, i.e. the same bending tube $3_1$, $3_2$, $3_3$, back to the shaft area. In each case, exactly the two base portions 6a, 6c of one of the three noose wires $5_1$, $5_2$, $5_3$ extends through each bending tube $3_1$, $3_2$, $3_3$.

In FIGS. 1 to 3, each noose arch 6b in the example shown extends, in the opened position of the snare structure 1, in a circular shape, substantially in a transverse plane perpendicular to the longitudinal direction of the instrument, parallel to a transverse plane in which the distal ends $4_1$, $4_2$, $4_3$ of the bending tubes $3_1$, $3_2$, $3_3$ lie. Thus, the noose arch 6b of each of the three noose wires $5_1$, $5_2$, $5_3$ extends with a circumferential length which is equal to the full 360° circumferential length of the snare structure 1 and which, in the depicted example of a snare structure with three bending tubes, accordingly corresponds to a circumferential length of three bending tube circumferential spacings. In other words, the noose arch $6b$ of the respective noose wire $5_1$, $5_2$, $5_3$ extends forwards from the distal end $4_1$, $4_2$, $4_3$ of the associated bending tube $3_1$, $3_2$, $3_3$ and, bending in the transverse plane direction, extends over the two other bending tubes or past the two other bending tubes and back again to the associated bending tube. In alternative embodiments, the noose arch of a respective noose wire extends over a circumferential angle of less than or more than 360°, and, in certain uses, it is also possible for a snare structure to use noose wires whose noose arches have different circumferential lengths.

In the illustrative embodiment of FIGS. 1 to 3, the noose arches $6b$ form an intersecting noose structure in which each noose arch $6b$ extends in a first portion in front of a first of the two other noose arches and extends in a second portion behind the first other noose arch. At the same time, in a further portion, it extends in front of the second of the two other noose arches and, in yet another portion, it extends behind this second of the two other noose arches. Overall, this leads to the intersecting noose structure depicted in FIGS. 1 to 3, one effect of which is that, when the snare structure 1 is contracted, a kind of knot 7 consisting of the intersecting noose arches $6b$ forms in the central area of the distal trap opening 2. The knot area 7 can advantageously serve to ensure that an object trapped in the snare is prevented from accidentally escaping from the contracted distal trap opening 2 of the snare. Moreover, the knot area 7 stabilizes the noose arches $6b$ in their mutual positioning. A further advantage of the intersecting noose structure is that the noose arch portions bearing against each other as a result of the intersecting provide a kind of shearing effect, by means of which, if necessary, the particles or concretions in tissue that are to be trapped can be more easily detached from an adherence to a tissue wall, for example.

To contract the snare structure 1 in the example in FIGS. 1 to 3, all the base portions $6a$, $6c$ of all the noose wires $5_1$, $5_2$, $5_3$ are arranged so as to be axially movable in the same direction and in synchrony and are guided in the bending tubes $3_1$, $3_2$, $3_3$. In this way, the noose arches $6b$ are configured to contract uniformly on both sides with which they open into the respectively associated bending tube $3_1$, $3_2$, $3_3$.

FIG. 4 illustrates one of the three noose wires used for the snare structure 1 in FIGS. 1 to 3, like the noose wire $5_1$ in its distal portion. FIG. 5 correspondingly shows the distal portion of a noose wire $5_4$, as can be used for a modified snare structure. In the noose wire $5_4$ of FIG. 5, the distal noose arch $6b$ does not extend, in the circumferential direction of the snare structure, over the full circumference of the snare, but instead only with a circumferential angle length of ca. 240°. In a snare structure with three bending tubes, this corresponds to a circumferential length of two bending tube circumferential spacings.

FIG. 6 shows two of three noose wires $5_4$ of the type from FIG. 5 which can be used to contract a snare structure with three bending tubes, for example the snare structure 1 from FIGS. 1 to 3. Of these bending tubes, the bending tube $3_1$ of this snare structure is shown schematically in FIG. 6. FIG. 7 shows the completed noose wire arrangement with the three noose wires $5_4$, which are arranged with their noose arches $6b$ offset from each other by in each case 120°. As can be seen for the bending tube $3_1$ in FIG. 6, each of the three bending tubes receives a first base portion $6a$ of one of the three noose wires $5_4$ and a second base portion $6c$ of another of the three noose wires $5_4$. The noose arches $6b$ in turn form an intersecting noose structure.

FIG. 8 shows a variant of the embodiment of the snare structure of FIGS. 6 and 7 having three double-lumen bending tubes $3_4$ are used as the bending tubes, of which one is shown in FIG. 8 with its distal end portion. The double-lumen bending tube $3_4$ has basically the shape of two single-lumen bending tubes bearing laterally against each other and connected to each other and configured in the manner of the bending tubes $3_1$, $3_2$, $3_3$ in the illustrative embodiments of FIGS. 1 to 7. The two associated noose wire base portions, i.e. the first base portion $6a$ of one of the noose wires and the second base portion $6c$ of another of the noose wires $5_4$, are guided loosely, and separate from each other, in the two lumens of the respective double-lumen bending tubes $3_4$. In this way, the two noose wire base portions $6a$, $6c$ guided in the same bending tube $3_4$ cannot adversely affect each other, and, in particular, no frictional effects arise as a result of the two noose wire base portions $6a$, $6c$ rubbing on each other.

As regards the shape of the distal noose arches of the noose wires applied in the various embodiments, some examplary embodiments are depicted in FIGS. 9 to 11. FIG. 9 shows the noose wire $5_1$ from FIG. 4 in a side view. As can be seen from this, the noose wire $5_1$ bends away from its base portion $6a$, which is to be received in a bending tube, with a relatively narrow curvature and substantially at right angles into a transverse plane which is perpendicular to the longitudinal direction of the instrument, and therefore to the axial direction or longitudinal direction of the snare structure, and in which it then extends with its noose arch $6b$. FIG. 10 shows one embodiment of a noose wire $5_5$ which, with a much wider curvature, i.e. with a radius of curvature much greater than the radius of curvature of the noose wire $5_1$ of the embodiment of FIG. 9, bends from the base portion $6a$, which extends substantially in the longitudinal direction of the instrument, into the noose arch portion $6b$, which extends in a plane perpendicular thereto. FIG. 11 shows another embodiment of a noose wire $5_6$ which, adjacent to its base portion $6a$, is curved through more than 90° and is thus bent back slightly before it merges into its noose arch portion $6b$. In the embodiment of FIG. 11, the bend from the base portion $6a$ to the noose arch portion $6b$ is ca. 180°.

FIG. 12 shows an embodiment wherein a noose wire $5_7$ which, on its noose arch portion $6b$, is provided with a nose-shaped bulge $6d$ on the side lying opposite the area of transition to the base portions $6a$, $6c$. This bulge $6d$ makes it easier to shorten the noose wire $5_7$, and in particular its noose arch $6b$ in order to contract the snare structure.

In the illustrative embodiments of FIGS. 1 to 7, the two relevant noose wire base portions $6a$, $6c$ are guided jointly, loosely and independently of each other in the respective bending tubes $3_1$, $3_2$, $3_3$. Alternatively, the noose wire base portions received in a respective bending tube can be connected to each other, for example by twisting, welding and/or adhesive bonding. In this connection, FIGS. 13 and 14 show two embodiments utilizing twisting.

FIG. 13 illustrates one embodiment of a noose wire arrangement for a snare structure as in the example of FIGS. 6 and 7, wherein the two base portions $6a$, $6c$ of the two noose wires $5_4$ to be received in a respective bending tube are twisted together. FIG. 14 shows an analogous twisting of the two base portions $6a$, $6c$ for the noose wire $5_1$ according to the embodiment of FIG. 4.

The connecting of the two noose wire base portions $6a$, $6c$, which are guided in a respective bending tube, can improve their guiding and stability in the bending tube and, if appropriate, in the shaft area of the instrument. Moreover, with this variant too, interactions between these two noose wire base portions 6a, 6c, such as rubbing against each other, can be avoided.

FIGS. 15 to 18 show a snare structure $1_1$ according to the embodiment of FIGS. 6 and 7, in a sequence that illustrates the trapping of a particle 8. The snare structure $1_1$ has the three bending tubes $3_1$, $3_2$, $3_3$ which, in the opened position of the snare structure $1_1$ in FIG. 15, extend distally forwards and radially and obliquely outwards. For the contraction at their distal ends $4_1$, $4_2$, $4_3$, the three noose wires $5_4$ are provided, of which the noose arches 6b extend, in the circumferential direction of the snare structure $1_1$, with a circumferential length of in each case two bending tube circumferential spacings and, therefore, of ca. 240°.

In operation, the snare structure $1_1$, in its opened position in FIG. 15, is moved axially forwards as a whole such that the object 8 to be trapped is introduced through the distal trap opening 2 into the snaring space delimited by the bending tubes $3_1$, $3_2$, $3_3$, as is shown in FIG. 16. Thereafter, the snare structure $1_1$ is contracted by means of the noose wires $5_4$ being moved axially rearwards with their base portions 6a, 6c relative to the bending tubes $3_1$, $3_2$, $3_3$. For this purpose, the noose wires $5_4$ are coupled with the proximal ends of their base portions 6a, 6c to the distal end of a pull rod 9 which, in a manner not shown in FIGS. 15 to 18, extends all the way through the shaft area of the instrument as far as a proximal control part of the instrument. FIG. 17 shows the snare structure $1_1$ in an intermediate position. FIG. 18 shows the snare structure $1_1$ in a contracted position in which the flexible bending tubes $3_1$, $3_2$, $3_3$ bear with tensioning against the outside of the trapped object 8 and thereby securely hold the latter. As a result of the intersecting arrangement of the noose arches 6b, a knot area $7_1$ is obtained in the central area of the distal trap opening 2, corresponding to the knot area 7 in the illustrative embodiment of FIGS. 1 to 3. In this way, the contracted noose arches 6b form a wire structure which shuts the trap opening 2 and by which the trapped object 8 is prevented from accidentally escaping from the trap opening 2.

In FIG. 19, the embodiment of FIGS. 15 to 18 is shown additionally with the pull rod 9 on the shaft side. The pull rod 9 can be made from any material known by a person skilled in the art to be suitable for this purpose, for uses with magnetic resonance (MR), e.g. from an MR-compatible, non-magnetic and electrically non-conductive material, such as a suitable plastic. The bending tubes $3_1$, $3_2$, $3_3$ can, for example, be made from a metal alloy known per se for such uses, for example a superelastic nickel-titanium alloy, or from a plastic hose material.

FIG. 20 shows one embodiment wherein the base portions 6a, 6c of the noose wires $5_4$ are twisted together and are continued rearwards all the way through the shaft portion as far as a proximal control part (not shown) of the instrument. The twisted noose wire base portions 6a, 6c extending all the way through the shaft portion may function as an alternative to the pull rod in the illustrative embodiment of FIG. 19.

FIG. 21 shows the embodiment of FIG. 19 in a contracted position of the snare structure $1_1$ similar to the position shown in FIG. 18, in which the snare structure $1_1$ securely holds the trapped object 8, such that the latter can be moved out of a human or animal tissue channel, for example. In FIG. 21, the instrument is supplemented by a shaft casing 10, in which the pull rod 9 and the noose wire base portions 6a, 6c extending rearwards and proximally from the bending tubes $3_1$, $3_2$, $3_3$ are received so as to be axially movable. When the trapped object 8 is to be released again, e.g. after it has been moved out of a tissue channel, the noose wires $5_4$ are moved axially forwards again, as a result of which the distal noose arches lengthen again. This allows the snare structure to open automatically, which is obtained by virtue of the fact that the flexible bending tubes return to their opened starting position on account of their inherent elasticity.

At their proximal end portion, the bending tubes $3_1$, $3_2$, are suitably fixed to each other and/or to a connection element provided at the distal end of the shaft portion of the instrument, as is known per se from the conventional snare instruments of the type in question. Alternatively, FIGS. 22 to 24 show further possible ways of fixing the bending tubes $3_1$, $3_2$, $3_3$. In the embodiment of FIG. 22, the aforementioned shaft casing 10 is connected directly, e.g. as a hose element, by adhesive bonding or shrink-fitting to the proximal end portions of the bending tubes $3_1$, $3_2$, $3_3$. In the embodiment of FIG. 23, the hose casing 10 is connected face-on to the proximal end portion of the bending tubes $3_1$, $3_2$, $3_3$ by means of an additional, surrounding connection sleeve 11, the connection once again being able to be effected by adhesive bonding or welding, for example.

In the embodiment of FIG. 24, the connection of shaft casing 10 and bending tubes $3_1$, $3_2$, $3_3$ is obtained, as in the example of FIG. 22, by direct insertion of the proximal ends of the bending tubes into the distal end area of the shaft casing 10 and by subsequent fixing, wherein an axially movable cover hose 12 is additionally provided which, particularly in the case of longer snare structures, can be used as an additional closing aid.

In embodiments, the snare structure of the snare instrument according to the present disclosure can be supplemented by a flexible snaring net structure, which is arranged in the snaring space formed by the bending tubes and is held on the bending tubes. FIGS. 25 to 29 show some illustrative embodiments of this, again using the example of a snare structure $1_2$ with the three bending tubes $3_1$, $3_2$, $3_3$ and the noose wires $5_4$ corresponding to the illustrative embodiments of FIGS. 15 to 24.

Figure 25:
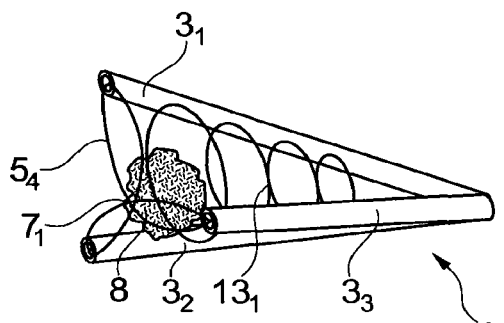
Figure 26:
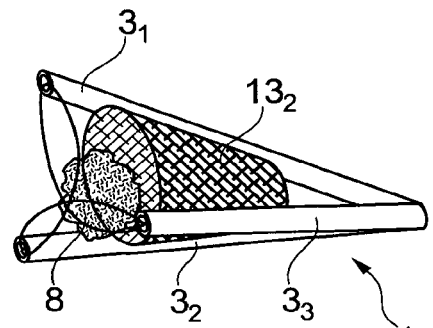

In the embodiment of FIG. 25, a helical wire spiral $13_1$ is introduced as flexible snaring net structure which, for example, can be made from the wire material of the noose wires $5_4$. The helical wire spiral $13_1$ widens conically in the distal direction, corresponding to the conical or funnel-shaped widening of the snaring space. In the embodiment of FIG. 26, a frustoconical lattice structure $13_2$ functions as a flexible snaring net structure in the funnel-shaped or conical snaring space.

Figure 27:
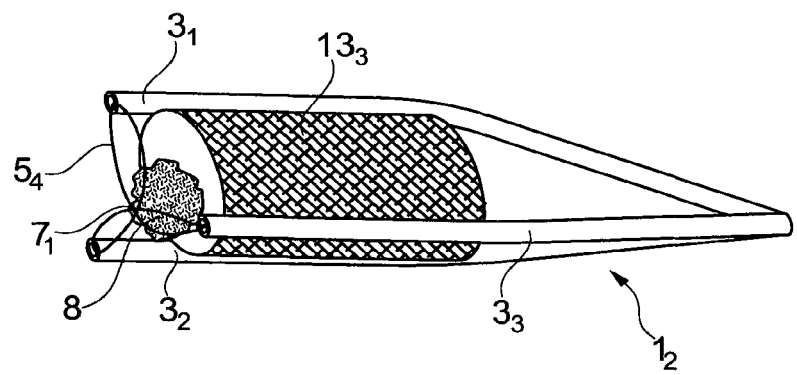

In the embodiment of FIG. 27, the bending tubes $3_1$, $3_2$, $3_3$ are slightly longer and form a cylindrical portion adjoining a conically widening portion of the snaring space. A cylindrical lattice $13_3$ is introduced as flexible snaring net structure into the cylindrical portion of the snaring space. Analogously, in the embodiment of FIG. 28, a cylindrical woven element $13_4$ is introduced into the cylindrical portion of the snaring space. As a further alternative, in the embodiment of FIG. 29 a cylindrical honeycomb woven element $13_5$ is introduced as flexible snaring net structure into the cylindrical portion of the snaring space.

In the embodiments of FIGS. 25 to 29, the distal trap opening is again closed off by the intersecting noose arches of the noose wires $5_4$ and by the resulting knot area $7_1$. In certain uses, the introduction of the flexible snaring net structure $13_1$ to $13_5$ can improve the trapping and securing characteristics of the snare structure $1_2$. The cylindrical snaring net structures $13_3$ to $13_5$ can, for example, be structures of the kind that are themselves known to a person skilled in the art from the field of medical stents. The snare instrument of the present disclosure could thus also serve to introduce stents into body tissue, while the snare structure is subsequently opened out and the instrument pulled back, in which process the stent can escape from the snaring space through the distal trap opening.

FIG. 30 illustrates an embodiment of the snare structure $1_1$ illustrated in the embodiments of FIGS. 15 to 19, in which the bending wires $3_1$, $3_2$, $3_3$ are each formed by a helical spring tube $14_1$, $14_2$, $14_3$. It will be appreciated that, in alternative configurations, it is also possible for just one or some of the bending tubes to be produced in this way from a helical spring tube material and for the one or more other bending tubes to be produced like those of the aforementioned illustrative embodiments, e.g. from monofilament wire tube material or from a plastic hose material.

FIG. 31 illustrates an embodiment of a snare structure with four bending tubes, and an arrangement of four noose wires $5_8$ which, with their noose arches $6b$, each extend by half the circumference of the snare and are not arranged intersecting.

Figure 32:
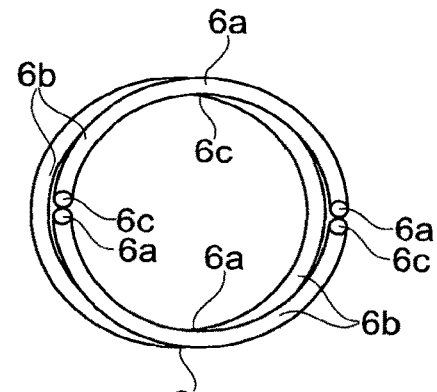
Figure 33:
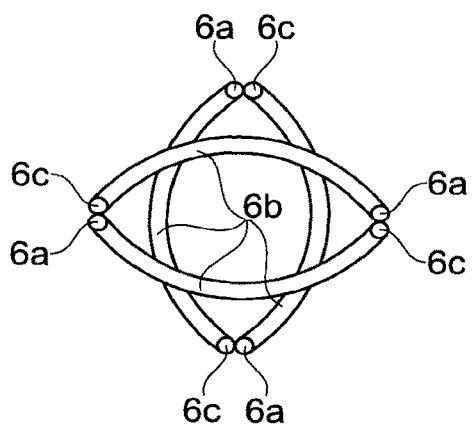
Figure 34:
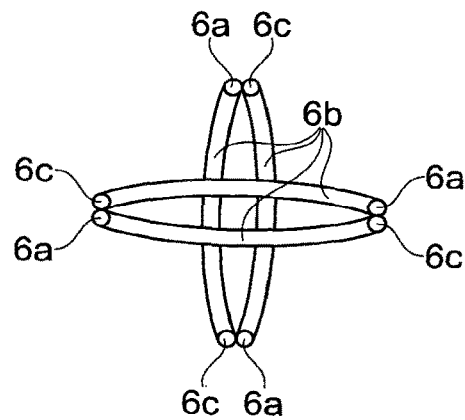
Figure 35:
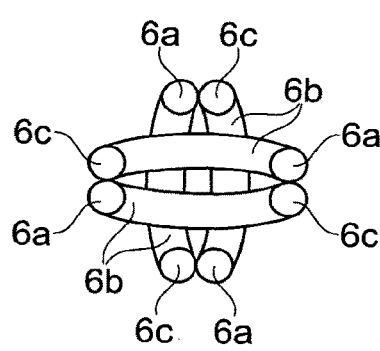
Figure 36:
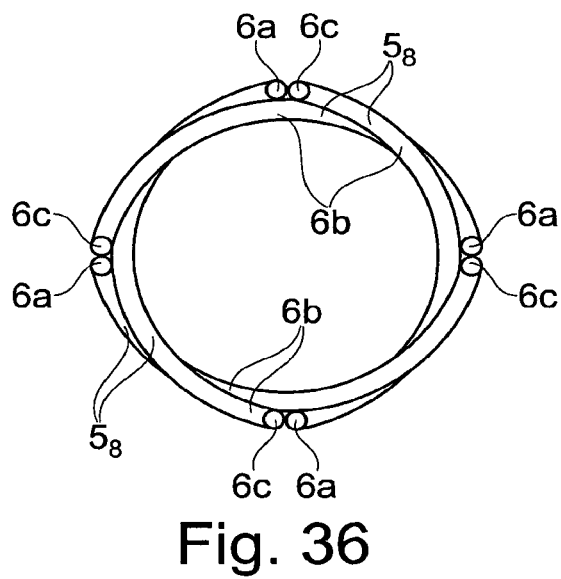
Figure 37:
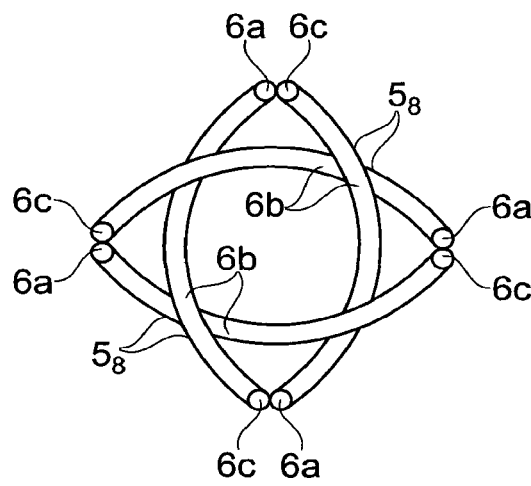
Figure 38:
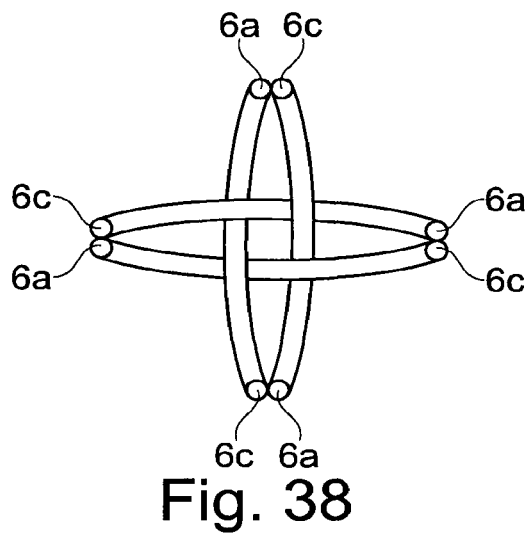
Figure 39:
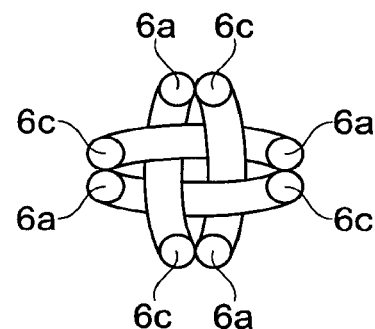

FIGS. 32 to 35 show plan views of the noose wire arrangement of the embodiment of FIG. 31 in increasingly further closed positions, starting from the fully opened position of FIGS. 31 and 32. As can be seen from the sequence of FIGS. 32 to 35, as the associated snare structure is pulled closed, the distal trap opening is increasingly narrowed and shut off by the contracting distal noose arches $6b$ of the noose wires $5_8$.

FIGS. 36 to 39 illustrate, in a sequence of contraction of the noose wires $5_8$ and of their distal noose arches $6b$ corresponding to the sequence of FIGS. 32 to 35, an embodiment in which the four noose wires $5_8$ are arranged with their four noose arches $6b$ intersecting each other. For this purpose, each noose wire $5_8$ extends, with its distal noose arch $6b$ between its two base portions $6a$, $6b$, in a first portion over, i.e. in front of the noose arch of a first of the three other noose arches and, in a second portion, below, i.e. behind the noose arch of a second of the three other noose arches.

Compared to the non-intersecting arrangement in the example of FIGS. 32 to 35, the embodiment according to FIGS. 36 to 39, with the intersecting arrangement of the noose arches $6b$, provides a shearing effect, which means that a particle that is to be trapped can more easily be detached from a tissue wall, for example. Moreover, the intersecting of the noose arches provides a weave-like cross-over of the noose arches $6b$ for closing the distal trap opening. On the other hand, under otherwise identical conditions for the embodiment of FIGS. 32 to 35, less tensile force has to be applied to contract the snare structure.

In the illustrative embodiments considered thus far, two noose wire base portions are received in each bending tube. However, the disclosure also concerns snare instruments in which only one noose wire base portion is received in one, several or all of the bending wires. FIGS. 40 to 43 show an illustrative embodiment of a snare structure with four bending tubes according to the illustrative embodiments of FIGS. 31 to 39.

In FIG. 40, the noose wire arrangement for the snare structure comprises two noose wires $5_9$ which, with their noose arch $6b$, extend in the circumferential direction of the snare structure by in each case three bending tube circumferential spacings and therefore over a circumferential length of ca. 270°. Each of the four noose wire base portions $6a$, $6c$ is received in its own bending tube.

FIGS. 41 to 43 illustrate the contraction behaviour of this noose wire arrangement with intersecting noose arches $6b$.

FIG. 41 shows the fully opened position corresponding to FIG. 40. FIG. 42 shows a contracted intermediate position, and FIG. 43 shows a substantially fully contracted position. As in other illustrative embodiments, the positions of the noose wire base portions $6a$, $6c$ shown in FIGS. 41 to 43 represent the position of the distal ends of the associated four bending tubes. As in the above illustrative embodiments, the bending tubes, at their distal ends, are configured to move radially inwards towards each other as a result of the contraction of the snare structure.

FIGS. 44 to 47 illustrate one embodiment of the noose wire arrangement of FIGS. 40 to 43 for a snare structure with six bending tubes in each of which, once again, only one noose wire base portion is received.

FIG. 44 shows a plan view of one of three used noose wires $5_{10}$, and FIG. 45 shows the associated arrangement of all three noose wires $5_{10}$ in an arrangement with intersecting noose arches $6b$. In this case, the noose arch $6b$ of each noose wire $5_{10}$ extends, in the circumferential direction of the snare structure, with a circumferential length of five bending tube circumferential spacings and therefore over a circumferential angle of ca. 300°. FIG. 46 shows an intermediate stage in the contraction of the noose arch arrangement, and FIG. 47 illustrates the noose arch arrangement in a practically fully contracted state. The distal ends of the bending wires, represented by the locations of the noose wire base portions $6a$, $6c$, are configured to move radially inwards towards each other by the contraction movement, so as to narrow the distal trap opening. In addition, the intersecting noose arch structure results in the formation of a noose knot $7_2$ in the central area of the distal trap opening, by means of which knot the trap opening is additionally closed off.

The embodiments with only one noose wire base portion in a respective bending tube permit a particularly small and light construction of the snare instrument and the use of bending wires with a relatively small diameter. Moreover, these variants are relatively simple to produce.

FIGS. 48 and 49 illustrate one embodiment of a snare instrument $1_3$ which is constructed from four bending wires $3_4$, $3_5$, $3_6$, $3_7$ which widen outwards in a funnel shape in the opened position of the snare. The snare instrument $1_3$ can be contracted by a noose wire arrangement, for which one of the noose wire arrangements of the embodiments of FIGS. 31 to 43 can be used, for example. Corresponding noose wires $5_{11}$ extend, from their distal noose arch portion, through the bending tubes $3_4$ to $3_7$ and, with subsequent twisting together, all the way through the shaft area of the instrument, surrounded by the shaft casing 10, as far as a proximal control part (not shown) of the instrument. From the opened position shown in FIG. 48, the snare structure $1_3$ can be contracted to its fully contracted position according to FIG. 49, in which its bending tubes $3_4$ to $3_7$ extend approximately parallel to the longitudinal direction of the instrument and the distal trap opening is largely closed.

FIG. 50 shows a further embodiment of the instrument from FIGS. 48 and 49, which has a snare structure $1_4$ with an additional cylindrical snaring space according to the illustrative embodiments of FIGS. 27 to 29. As in the illustrative embodiment of FIG. 24, the shaft casing 10 is additionally equipped with an axially movable cover hose or cover tube 12. FIG. 50 shows the instrument in the fully opened position of the snare structure $1_4$.

FIG. 51 shows the instrument of FIG. 50 in a position of the snare structure $1_4$ in which the noose wires $5_{11}$ are axially pulled back to the full extent. On account of the bulbous shape and the relatively long length of the snare structure $1_4$, a slight residual bulging of the snare structure $1_4$ remains, which can be further compressed with the aid of the cover tube 12. For this purpose, the cover tube 12 is moved axially forwards, as is illustrated in FIG. 52. In this way, the cover tube 12 supports the closing of the snare structure $1_4$ otherwise brought about by the axial retraction of the noose wires $5_8$. This supporting closing action provided by the axially movable cover hose 12 is especially advantageous in the case of longer instruments and/or bulbous snare structures like the snare structure $1_4$ in FIGS. 50 to 52. By this means, the tensile forces and the tensile loads for the noose wires $5_8$ can be kept relatively low. This applies particularly in the case where a flexible snaring net structure is additionally introduced into the snaring space of the snare structure, like one of the net structures $13_1$ to $13_5$ of FIGS. 25 to 29, which has to be pressed together to contract the snare structure.

The illustrative embodiments of the above disclosure provides a snare instrument with an advantageous snare structure which can be contracted by a noose wire arrangement in which the noose arch of at least one of the noose wires extends, at the distal area of the snare structure, with a circumferential length of at least two bending tube circumferential spacings in the circumferential direction of the snare structure. This favours the contraction of the snare structure and of its distal trap opening, and the closure of the latter against inadvertent escape of objects that are trapped in the snaring space. It will be appreciated that further alternative embodiments of the snare instrument according to the invention can be realized from combinations of the illustrated measures described above, as will be readily apparent to a person skilled in the art.

The invention claimed is:

1. An endoscopic instrument providing a flexible three-arm snare structure adapted to retrieve stones from a human body, the endoscopic instrument comprising:
   a shaft;
   three double-lumen bending tubes disposed in the shaft, with the three double-lumen bending tubes including a first double-lumen bending tube and a second double-lumen bending tube and a third double-lumen bending tube each spaced around an inner circumference of the shaft and separated from an adjacent one of the three double-lumen bending tubes; and
   a snare structure coupled with the three double-lumen bending tubes, the snare structure comprising a first noose wire and a second noose wire and a third noose wire;
   wherein the first noose wire has a first base portion retained in a first lumen of the first double-lumen bending tube, a first wire segment extending from the first base portion to a second base portion, with the second base portion retained in a second lumen of the second double-lumen bending tube;
   wherein the second noose wire has a first base portion retained in a first lumen of the second double-lumen bending tube, a second wire segment extending from the first base portion to a second base portion, with the second base portion retained in a second lumen of the third double-lumen bending tube;
   wherein the third noose wire has a first base portion retained in a first lumen of the third double-lumen bending tube, a third wire segment extending from the first base portion to a second base portion, with the second base portion retained in a second lumen of the first double-lumen bending tube.

2. The endoscopic instrument of claim 1, wherein the first base portion of the first noose wire and the second base portion of the third noose wire are separated from contact and guided within the first double-lumen bending tube.

3. The endoscopic instrument of claim 1, wherein the first base portion of the first noose wire and the second base portion of the third noose wire are movable within the first double-lumen bending tube.

4. The endoscopic instrument of claim 1, wherein the first base portion of the first noose wire and the second base portion of the third noose wire extend axially within the first double-lumen bending tube such that the first base portion of the first noose wire and the second base portion of the third noose wire are movable in a same direction and in synchrony within the first double-lumen bending tube.

5. The endoscopic instrument of claim 1, wherein the first base portion of the first noose wire is separated from the second base portion of the third noose wire within the first double-lumen bending tube and so adapted to prevent rubbing of the first base portion of the first noose wire against the second base portion of the third noose wire.

6. The endoscopic instrument of claim 1, wherein the first double-lumen bending tube is adapted to prevent friction between the first base portion of the first noose wire and the second base portion of the third noose wire that are retained in the first double-lumen bending tube.

7. The endoscopic instrument of claim 1, wherein the first noose wire and the second noose wire and the third noose wire extend proximally through the shaft away from the snare structure to a proximal control area of the endoscopic instrument.

8. The endoscopic instrument of claim 1, wherein the snare structure is a flexible snaring net structure that forms a snaring space between the three double-lumen bending tubes.

9. A method of retrieving stones out of a human body, the method comprising:
   providing a flexible three-arm snare structure having three double-lumen bending tubes disposed in a shaft, with the three double-lumen bending tubes including a first double-lumen bending tube and a second double-lumen bending tube and a third double-lumen bending tube each spaced around an inner circumference of the shaft and separated from an adjacent one of the three double-lumen bending tubes; and a snare structure coupled with the three double-lumen bending tubes, the snare structure comprising a first noose wire and a second noose wire and a third noose wire, with: the first noose wire having a first base portion retained in a first lumen of the first double-lumen bending tube, a first wire segment extending from the first base portion to a second base portion, and the second base portion retained in a second lumen of the second double-lumen bending tube; the second noose wire having a first base portion retained in a first lumen of the second double-lumen bending tube, a second wire segment extending from the first base portion to a second base portion, and the second base portion retained in a second lumen of the third double-lumen bending tube; the third noose wire having a first base portion retained in a first lumen of the third double-lumen bending tube, a third wire segment extending from the first base portion to a second base portion, and the second base portion retained in a second lumen of the first double-lumen bending tube;
   inserting the flexible three-arm snare structure into the human body;

extending the first base portion of the first noose wire and the second base portion of the third noose wire axially in a distal direction out of the first double-lumen bending tube to form a snaring space with the second noose wire;

capturing a stone in the snaring space;

retracting the first base portion of the first noose wire and the second base portion of the third noose wire axially in a proximal direction into the first double-lumen bending tube to close the snaring space; and removing the flexible three-arm snare structure and the stone from the human body.

\* \* \* \* \*